(12) United States Patent
Miller, II et al.

(10) Patent No.: US 12,188,847 B2
(45) Date of Patent: Jan. 7, 2025

(54) TIME-AND DATA-EFFICIENT ASSURANCE OF LEAK DETECTION

(71) Applicant: SeekOps Inc., Austin, TX (US)

(72) Inventors: Victor Alexander Miller, II, Austin, TX (US); Stuart Buckingham, Austin, TX (US); Brendan James Smith, Lakeway, TX (US); Michael Price McGuire, Austin, TX (US)

(73) Assignee: SeekOps Inc., Austin, TX (US)

( * ) Notice: Subject to any disclaimer, the term of this patent is extended or adjusted under 35 U.S.C. 154(b) by 416 days.

(21) Appl. No.: 17/601,559

(22) PCT Filed: Apr. 1, 2020

(86) PCT No.: PCT/US2020/026232
§ 371 (c)(1),
(2) Date: Oct. 5, 2021

(87) PCT Pub. No.: WO2020/206008
PCT Pub. Date: Oct. 8, 2020

(65) Prior Publication Data
US 2022/0170810 A1 Jun. 2, 2022

Related U.S. Application Data

(60) Provisional application No. 62/829,752, filed on Apr. 5, 2019.

(51) Int. Cl.
*G01M 3/04* (2006.01)
*G01C 21/20* (2006.01)
*G01S 19/01* (2010.01)

(52) U.S. Cl.
CPC .............. *G01M 3/04* (2013.01); *G01C 21/20* (2013.01); *G01S 19/01* (2013.01)

(58) Field of Classification Search
CPC ........... G01M 3/04; G01C 21/20; G01S 19/01
(Continued)

(56) References Cited

U.S. PATENT DOCUMENTS 3,780,566 A 12/1973 Smith et al.
4,135,092 A 1/1979 Milly
(Continued)

FOREIGN PATENT DOCUMENTS

AU 3401499 A 11/1999
CN 101470072 A 7/2009
(Continued)

OTHER PUBLICATIONS

International Search Report and Written Opinion for PCT/US2023/023933 mailed Sep. 26, 2023.
(Continued)

*Primary Examiner* — Kerri L McNally
(74) *Attorney, Agent, or Firm* — Command IP LLP; Michael Zarrabian

(57) ABSTRACT

Systems, devices, and methods including an aerial vehicle having a global positioning system (GPS) and at least one trace-gas sensor configured to generate gas data; and a processor having addressable memory, the processor configured to: determine a flight envelope based on a received spatial location, a received spatial location of the one or more potential gas sources, a received desired level of confidence, and a received wind data; determine a flight path for the aerial vehicle, where the flight path covers a portion of the determined flight envelope; and determine based on a received gas data whether a gas leak is present in the received spatial location to the received desired level of confidence.

17 Claims, 14 Drawing Sheets

(58) Field of Classification Search
USPC .................................................... 340/979
See application file for complete search history.

(56) References Cited

U.S. PATENT DOCUMENTS

| | | | |
|---|---|---|---|
| 4,233,564 A | 11/1980 | Kerbel | |
| 4,507,558 A | 3/1985 | Bonne | |
| 4,988,833 A | 1/1991 | Lai | |
| 5,047,639 A | 9/1991 | Wong | |
| 5,075,619 A | 12/1991 | Said | |
| 5,173,749 A | 12/1992 | Tell et al. | |
| 5,291,265 A | 3/1994 | Kebabian | |
| 5,317,156 A | 5/1994 | Cooper et al. | |
| 5,767,780 A | 6/1998 | Smith et al. | |
| 5,822,058 A | 10/1998 | Adler-Golden et al. | |
| 6,064,488 A | 5/2000 | Brand et al. | |
| 6,295,859 B1 | 10/2001 | Hayden et al. | |
| 6,356,350 B1 | 3/2002 | Silver et al. | |
| 6,509,566 B1 | 1/2003 | Wamsley et al. | |
| 6,549,630 B1 | 4/2003 | Bobisuthi | |
| 7,162,933 B2 | 1/2007 | Thompson et al. | |
| 7,800,751 B1 | 9/2010 | Silver et al. | |
| 7,833,480 B2 | 11/2010 | Blazewicz et al. | |
| 8,060,270 B2 | 11/2011 | Vian et al. | |
| 8,294,899 B2 | 10/2012 | Wong | |
| 8,451,120 B2 | 5/2013 | Johnson, Jr. et al. | |
| 8,730,461 B2 | 5/2014 | Andreussi | |
| 9,183,371 B2 | 11/2015 | Narendra et al. | |
| 9,183,731 B1 | 11/2015 | Bokhary | |
| 9,235,974 B2 | 1/2016 | Johnson, Jr. et al. | |
| 9,250,175 B1 | 2/2016 | McManus | |
| 9,494,511 B2 | 11/2016 | Wilkins | |
| 9,599,529 B1 | 3/2017 | Steele et al. | |
| 9,599,597 B1 | 3/2017 | Steele et al. | |
| 10,023,311 B2 | 7/2018 | Lai et al. | |
| 10,023,323 B1 | 7/2018 | Roberts et al. | |
| 10,031,040 B1 | 7/2018 | Smith et al. | |
| 10,126,200 B1* | 11/2018 | Steele | G01N 33/0075 |
| 10,268,198 B2 | 4/2019 | Mantripragada et al. | |
| 10,325,485 B1 | 6/2019 | Schuster | |
| 10,365,646 B1 | 7/2019 | Farnsworth et al. | |
| 10,429,546 B1 | 10/2019 | Ulmer | |
| 10,677,771 B2 | 6/2020 | Dittberner et al. | |
| 10,753,864 B2 | 8/2020 | Kasten et al. | |
| 10,816,458 B2 | 10/2020 | Kasten et al. | |
| 10,830,034 B2 | 11/2020 | Cooley et al. | |
| 10,962,437 B1 | 3/2021 | Nottrott et al. | |
| 11,105,784 B2 | 8/2021 | Kukreja et al. | |
| 11,112,308 B2 | 9/2021 | Kreitinger et al. | |
| 11,275,068 B2 | 3/2022 | Willett | |
| 11,299,268 B2 | 4/2022 | Christensen et al. | |
| 11,519,855 B2 | 12/2022 | Black et al. | |
| 11,557,212 B2 | 1/2023 | Hong | |
| 11,614,430 B2 | 3/2023 | Buckingham et al. | |
| 11,619,562 B2 | 4/2023 | Leen et al. | |
| 11,710,411 B2 | 7/2023 | Van Meeteren et al. | |
| 11,748,866 B2 | 9/2023 | Vargas | |
| 2002/0005955 A1 | 1/2002 | Kramer et al. | |
| 2003/0160174 A1 | 8/2003 | Grant et al. | |
| 2003/0189711 A1 | 10/2003 | Orr et al. | |
| 2003/0230716 A1 | 12/2003 | Russell et al. | |
| 2004/0012787 A1 | 1/2004 | Galle et al. | |
| 2004/0017762 A1 | 1/2004 | Sogawa et al. | |
| 2004/0212804 A1 | 10/2004 | Neff et al. | |
| 2006/0015290 A1 | 1/2006 | Warburton et al. | |
| 2006/0044562 A1 | 3/2006 | Hagene et al. | |
| 2006/0232772 A1 | 10/2006 | Silver | |
| 2006/0234621 A1 | 10/2006 | Desrochers et al. | |
| 2007/0137318 A1 | 6/2007 | Desrochers et al. | |
| 2008/0169934 A1 | 7/2008 | Lang et al. | |
| 2008/0243372 A1 | 10/2008 | Bodin et al. | |
| 2009/0201507 A1 | 8/2009 | Kluczynski et al. | |
| 2009/0263286 A1 | 10/2009 | Isomura et al. | |
| 2009/0326792 A1 | 12/2009 | McGrath | |
| 2010/0004798 A1 | 1/2010 | Bodin et al. | |
| 2010/0131207 A1 | 5/2010 | Lippert et al. | |
| 2010/0140478 A1 | 6/2010 | Wilson et al. | |
| 2010/0147081 A1 | 6/2010 | Thomas | |
| 2011/0035149 A1 | 2/2011 | McAndrew et al. | |
| 2011/0074476 A1 | 3/2011 | Heer et al. | |
| 2011/0150035 A1 | 6/2011 | Hanson et al. | |
| 2011/0164251 A1 | 7/2011 | Richter | |
| 2011/0213554 A1 | 9/2011 | Archibald et al. | |
| 2011/0257944 A1 | 10/2011 | Du et al. | |
| 2012/0120397 A1 | 5/2012 | Furtaw et al. | |
| 2013/0044314 A1 | 2/2013 | Koulikov et al. | |
| 2013/0076900 A1 | 3/2013 | Mrozek et al. | |
| 2013/0208262 A1 | 8/2013 | Andreussi | |
| 2014/0172323 A1 | 6/2014 | Marino | |
| 2014/0204382 A1 | 7/2014 | Christensen | |
| 2014/0236390 A1* | 8/2014 | Mohamadi | B64C 39/024 701/16 |
| 2014/0336957 A1 | 11/2014 | Hanson et al. | |
| 2015/0072633 A1 | 3/2015 | Massarella et al. | |
| 2015/0145954 A1 | 5/2015 | Pulleti et al. | |
| 2015/0226575 A1 | 8/2015 | Rambo | |
| 2015/0275114 A1 | 10/2015 | Tumiatti et al. | |
| 2015/0295543 A1 | 10/2015 | Brown et al. | |
| 2015/0316473 A1 | 11/2015 | Kester et al. | |
| 2015/0323449 A1 | 11/2015 | Jones et al. | |
| 2015/0336667 A1 | 11/2015 | Srivastava et al. | |
| 2016/0018373 A1 | 1/2016 | Pagé et al. | |
| 2016/0070265 A1 | 3/2016 | Liu et al. | |
| 2016/0104250 A1 | 4/2016 | Allen et al. | |
| 2016/0146696 A1 | 5/2016 | Steele et al. | |
| 2016/0161456 A1 | 6/2016 | Risk et al. | |
| 2016/0202225 A1 | 7/2016 | Feng et al. | |
| 2016/0214715 A1* | 7/2016 | Meffert | B64D 47/08 |
| 2016/0307447 A1 | 10/2016 | Johnson et al. | |
| 2016/0357192 A1 | 12/2016 | McGrew et al. | |
| 2017/0003684 A1* | 1/2017 | Knudsen | G07C 5/008 |
| 2017/0057081 A1 | 3/2017 | Krohne et al. | |
| 2017/0089829 A1 | 3/2017 | Bartholomew et al. | |
| 2017/0093122 A1 | 3/2017 | Bean et al. | |
| 2017/0097274 A1 | 4/2017 | Thorpe et al. | |
| 2017/0115218 A1 | 4/2017 | Huang et al. | |
| 2017/0134497 A1 | 5/2017 | Harter et al. | |
| 2017/0158353 A1 | 6/2017 | Schmick | |
| 2017/0199647 A1 | 7/2017 | Richman et al. | |
| 2017/0206648 A1 | 7/2017 | Marra et al. | |
| 2017/0235018 A1 | 8/2017 | Foster et al. | |
| 2017/0259920 A1 | 9/2017 | Lai et al. | |
| 2017/0307519 A1 | 10/2017 | Black et al. | |
| 2017/0336281 A1 | 11/2017 | Waxman et al. | |
| 2017/0339820 A1 | 11/2017 | Foster et al. | |
| 2018/0023974 A1 | 1/2018 | Otani et al. | |
| 2018/0024091 A1 | 1/2018 | Wang et al. | |
| 2018/0045561 A1 | 2/2018 | Leen et al. | |
| 2018/0045596 A1 | 2/2018 | Prasad et al. | |
| 2018/0050798 A1 | 2/2018 | Kapuria | |
| 2018/0059003 A1 | 3/2018 | Jourdainne et al. | |
| 2018/0067066 A1 | 3/2018 | Giedd et al. | |
| 2018/0109767 A1 | 4/2018 | Li et al. | |
| 2018/0122246 A1 | 5/2018 | Clark | |
| 2018/0127093 A1 | 5/2018 | Christensen et al. | |
| 2018/0188129 A1 | 7/2018 | Choudhury et al. | |
| 2018/0209902 A1 | 7/2018 | Myshak et al. | |
| 2018/0259955 A1 | 9/2018 | Noto | |
| 2018/0266241 A1 | 9/2018 | Ferguson et al. | |
| 2018/0266946 A1 | 9/2018 | Kotidis et al. | |
| 2018/0284088 A1 | 10/2018 | Verbeck, IV | |
| 2018/0292834 A1* | 10/2018 | Dittberner | G05D 1/0088 |
| 2018/0321692 A1 | 11/2018 | Castillo-Effen et al. | |
| 2018/0322699 A1 | 11/2018 | Gray et al. | |
| 2019/0011920 A1 | 1/2019 | Heinonen et al. | |
| 2019/0011935 A1 | 1/2019 | Ham et al. | |
| 2019/0025199 A1 | 1/2019 | Koulikov | |
| 2019/0033194 A1 | 1/2019 | DeFreez et al. | |
| 2019/0049364 A1 | 2/2019 | Rubin | |
| 2019/0077506 A1 | 3/2019 | Shaw et al. | |
| 2019/0086202 A1 | 3/2019 | Guan et al. | |
| 2019/0095687 A1 | 3/2019 | Shaw et al. | |
| 2019/0154874 A1 | 5/2019 | Shams et al. | |
| 2019/0178743 A1 | 6/2019 | McNeil | |

(56) References Cited

U.S. PATENT DOCUMENTS

| | | | |
|---|---|---|---|
| 2019/0195789 | A1 | 6/2019 | Pan et al. |
| 2019/0204189 | A1 | 7/2019 | Mohr, Jr. et al. |
| 2019/0212419 | A1 | 7/2019 | Jeong et al. |
| 2019/0220019 | A1 | 7/2019 | Tan et al. |
| 2019/0228573 | A1 | 7/2019 | Sen et al. |
| 2019/0234868 | A1 | 8/2019 | Tanomura et al. |
| 2019/0331652 | A1 | 10/2019 | Ba et al. |
| 2020/0050189 | A1 | 2/2020 | Gu et al. |
| 2020/0065433 | A1 | 2/2020 | Duff et al. |
| 2020/0109976 | A1 | 4/2020 | Ajay et al. |
| 2020/0135036 | A1 | 4/2020 | Campbell |
| 2020/0182779 | A1 | 6/2020 | Kasten et al. |
| 2020/0249092 | A1 | 8/2020 | Podmore et al. |
| 2020/0373172 | A1 | 11/2020 | Suzuki |
| 2020/0400635 | A1 | 12/2020 | Potyrailo et al. |
| 2021/0017926 | A1 | 1/2021 | Alkadi et al. |
| 2021/0037197 | A1 | 2/2021 | Kester et al. |
| 2021/0055180 | A1 | 2/2021 | Thorpe et al. |
| 2021/0109074 | A1 | 4/2021 | Smith et al. |
| 2021/0140934 | A1 | 5/2021 | Smith et al. |
| 2021/0190745 | A1 | 6/2021 | Buckingham et al. |
| 2021/0190918 | A1 | 6/2021 | Li et al. |
| 2021/0199565 | A1 | 7/2021 | John et al. |
| 2021/0247369 | A1 | 8/2021 | Nottrott et al. |
| 2021/0255158 | A1 | 8/2021 | Smith et al. |
| 2021/0300591 | A1 | 9/2021 | Tian |
| 2021/0321174 | A1 | 10/2021 | Sun et al. |
| 2021/0364427 | A1 | 11/2021 | Smith et al. |
| 2021/0382475 | A1 | 12/2021 | Smith et al. |
| 2022/0082495 | A1 | 3/2022 | Kreitinger et al. |
| 2022/0113290 | A1 | 4/2022 | Smith et al. |
| 2022/0170810 | A1 | 6/2022 | Miller, II et al. |
| 2022/0268952 | A1 | 8/2022 | Liang et al. |
| 2022/0341806 | A1 | 10/2022 | Miller et al. |
| 2022/0357231 | A1 | 11/2022 | Nahata et al. |
| 2023/0194487 | A1 | 6/2023 | Buckingham et al. |
| 2023/0213413 | A1 | 7/2023 | Mohr, Jr. et al. |
| 2023/0274651 | A1 | 8/2023 | McGuire et al. |
| 2023/0392498 | A1 | 12/2023 | Srivastav et al. |

FOREIGN PATENT DOCUMENTS

| | | | |
|---|---|---|---|
| CN | 104458588 | A | 3/2015 |
| CN | 205749271 | U | 11/2016 |
| CN | 106568516 | A | 4/2017 |
| CN | 106769977 | A | 5/2017 |
| CN | 107703075 | A | 2/2018 |
| CN | 109780452 | A | 5/2019 |
| CN | 211508182 | U | 9/2020 |
| CN | 112213443 | A | 1/2021 |
| DE | 29601472 | U1 | 5/1996 |
| DE | 69333010 | | 4/2004 |
| DE | 102014013822 | A1 | 3/2016 |
| EP | 0450809 | A2 | 10/1991 |
| EP | 1371962 | B1 | 7/2011 |
| EP | 3339855 | A1 | 6/2018 |
| FR | 3047073 | A1 | 7/2017 |
| FR | 3047073 | B1 | 8/2019 |
| GB | 2538563 | A | 11/2016 |
| JP | H08247939 | A | 9/1996 |
| JP | 200975823 | A | 4/2009 |
| KR | 20170062813 | A | 6/2017 |
| KR | 101770254 | B1 | 8/2017 |
| TW | 522226 | B | 3/2003 |
| WO | 1999054700 | A2 | 10/1999 |
| WO | 02066950 | A1 | 8/2002 |
| WO | 2008021311 | A2 | 2/2008 |
| WO | 2015073687 | A1 | 5/2015 |
| WO | 2016045791 | A1 | 3/2016 |
| WO | 2016162673 | A1 | 10/2016 |
| WO | 2017069979 | A1 | 4/2017 |
| WO | 2018121478 | A1 | 7/2018 |
| WO | 2018227153 | A1 | 12/2018 |
| WO | 2019246280 | A1 | 12/2019 |
| WO | 2020007684 | A1 | 1/2020 |
| WO | 2020028353 | A1 | 2/2020 |
| WO | 2020086499 | A1 | 4/2020 |
| WO | 2020206006 | A1 | 10/2020 |
| WO | 2020206008 | A1 | 10/2020 |
| WO | 2020206020 | A1 | 10/2020 |
| WO | 2021055902 | A1 | 3/2021 |
| WO | 2021158916 | A1 | 8/2021 |
| WO | 2022093864 | A1 | 5/2022 |
| WO | 2022211837 | A1 | 10/2022 |

OTHER PUBLICATIONS

U.S. Appl. No. 62/687,147, filed Jun. 19, 2018, Brendan James Smith.

"Safesite Multi-Threat Detection System", Jul. 11, 2012 (Jul. 11, 2012), pp. 1-6, XP055245980.

International Search Report and Written Opinion for PCT/US19/38011 mailed Sep. 9, 2019.

International Search Report and Written Opinion for PCT/US19/38015, mailed Oct. 18, 2019.

International Search Report and Written Opinion for PCT/US19/44119, mailed Oct. 17, 2019.

International Search Report and Written Opinion for PCT/US20/26228 mailed Jul. 1, 2020.

International Search Report and Written Opinion for PCT/US20/26246 mailed Jun. 29, 2020.

International Search Report and Written Opinion for PCT/US20/51696, mailed Feb. 3, 2021.

International Search Report and Written Opinion for PCT/US2020/044978, mailed Oct. 26, 2020.

International Search Report and Written Opinion for PCT/US2021/016821 mailed Apr. 26, 2021.

International Search Report and Written Opinion for PCT/US2021/024177, mailed Jun. 23, 2021.

International Search Report and Written Opinion for PCT/US2021/056708, mailed Jan. 27, 2022.

International Search Report and Written Opinion for PCT/US21/42061, mailed Nov. 26, 2021.

International Search Report and Written Opinion for PCT/US21/44532, mailed Jan. 11, 2022.

International Search Report and Written Opinion for PCT/US21/56710, mailed Feb. 23, 2022.

International Search Report and Written Opinion of PCT/US19/57305, mailed Jan. 2, 2020.

International Search Report and Written Opinion of PCT/US20/54117, mailed Dec. 22, 2020.

Joly, "Atmospheric Measurements by Ultra-Light Spectrometer (AMULSE) Dedicated to Vertical Profile In Situ Measurements of Carbon Dioxide ($CO_2$) Under Weather Balloons: Instrumental Development and Field Application," Sensors 2016, 16, 1609.

Khan, "Low Power Greenhouse Gas Sensors for Unmanned Aerial Vehicles", Remote Snse. 2012, 4, 1355-1368.

Villla. "An Overview of Small Unmanned Aerial Vehicles for Air Quality Measurements: Present Applications and Future Prospectives". Sensors. Web . Jul. 12, 2016.

White, "Development of an Unmanned Aerial Vehicle for the Measurement of Turbulence in the Atmospheric Boundary Layer", Atmosphere, v.8, issue 10, 195, pp. 1-25.

Lilian Joly, The evolution of AMULSE (Atmospheric Measurements by Ultra-Light Spectrometer) and its interest in atmospheric applications. Results of the Atmospheric Profiles of GreenhousE gasEs (APOGEE) weather balloon release campaign for satellite retrieval validation, p. 1-28, Sep. 25, 2019, Atmospheric Measurement Techniques Discussion (Joly).

International Search Report and Written Opinion for PCT/US23/13893, mailed Jun. 30, 2023.

Clilverd, Mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).

(56) References Cited

OTHER PUBLICATIONS

Kem, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).

Liao, J. et al. Observations of Inorganic bromine(HOBr, BrO, and Br2) speciation at Barrow, Alaska in spring 2009, Journal of Geophysical Research, vol. 117, D00R16, doi:10.1029/2011JD016641, 2012, pp. 1-11 (Year:2012).

Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).

Miyama, Toru et al., Estimating allowable carbon emission for CO2 concentration stabilization using a GCM-based Earth system model, Geophysical Research Letters, vol. 36,L19709, doi:10.1029/2009GL039678, 2009, pp. 0094-8276 (Year:2009).

Oppenheimer Clive et al., Ultraviolet Sensing of Volcanic Sulfur Emissions, Elements (An Internatioknal Magazine of Mineralogy, Geochemistry, and Petrology), Apr. 2010, vol. 6, pp. 87-92 (Year: 2010).

Parazoo, Nicholas C. et al., Interpreting seasonal changes in the carbon balance of southern Amazonia using measurements of XCO2 and chlorophyll fluorescence from GOSAT, Geophysical Research Letters, vol. 40.2829-2833, doi: 10.1002/grl.50452, 2013 pp. 2829-2833 (Year:2013).

Queiber, Manuel et al., A new frontier in CO2 flux measurements using a highly portable DIAL laser system, Scientific Reports, DOI: 10.1038/srep33834 1, Sep. 22, 2016, pp. 1-13(Year:2016).

Queiber, Manuel et al., Large-area quantification of subaerial CO2 anomalies with portable laser remote sensing and 2d tomography, The Leading Edge Mar. 2018, pp. 306-313 (Year:2018).

International Search Report and Written Opinion for PCT/US20/26232 mailed Jun. 26, 2020.

IEEE Conference Paper, "Research of the high pressure jet performance of small size nozzle," ISBN :978-1-5090-1087-5,Publication Date : Oct. 1, 2016, Conference dates Oct. 10, 2016 thru Oct. 12, 2016.[retrieved from the Internet] on Sep. 1, 2023 at 4:14pm.

Development of a mobile tracer correlation method for assessment of air emissions from landfills and other area sources, Atmospheric Environment 102 (2015) 323-330. T.A. Foster-Wittig et. al. 2015.

Measurements of Methane Emissions from Landfills Using a Time Correlation Tracer Method Based on FTIR Absorption Spectroscopy, Environ. Sci. Technol. 2001, 35, 21-25, B. Galle et. al. 2001.

International Search Report and Written Opinion for PCT/US23/23905 mailed Oct. 5, 2023.

International Search Report and Written Opinion for PCT/US22/38951, mailed Nov. 28, 2022.

Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.

Krings et al., Atmos. Meas. Tech., 11, 721-739, Feb. 7, 2018.

Cabreira et al. "Survey on Coverage Path Planning with Unmanned Aerial Vehicles", published: Drones, published: Jan. 2019, pp. 1-38, year 2019.

Feng, Lingbing, Nowak, Gen, O'Neill, T.J., Welsh, A.H."CUTOFF; A spatio-temporal imputation method." Journal of Hydrology 519 (2014) : 3591-3605 (Year:2014).

Coombes et al, "Optimal Polygon Decomposition for UAV Survey Coverage Path Planning in Wind", published: Jul. 2018, publisher: 'Sensors' (Year:2018).

He et al. "Static Targets' Track Path for UAVs Meeting the Revisit Interval Requirement", published :2013, publisher : IEEE (Year:2013).

Field Trial of Methane Emission Quantification Technologies, Society of Petroleum Engineers, SPE-201537-MS, Allen et al., Oct. 2020.

Tao Lei et al:" Low-power, open-path mobile sensing platform for high-resolution measurements of greenhouse gases and air pollutants", Applied Physics B, Springer Berlin Heidelberg, Berlin/Heidelberg, vol. 119, No. 1, Mar. 10, 2015 (Mar. 10, 2015), pp. 153-164, XP035445836, ISSN: 0946-2171, DOI:10.1007/ S00340-015-6069-1 [retrieved on Mar. 10, 2015].

Tarsitano C G et al: Multilaser Herriott Cell for Planetary Tunable Laser Spectrometers', Applied Optics , Optical Society of America, Washington, DC, US, vol. 46, No. 28, Oct. 1, 2007 (Oct. 1, 2007), pp. 6923-6935, XP001508502, ISSN:0003-6935, DOI: 10.1364/AO.46.006923.

Uehara, K: "Dependence of harmonic signals 1-15 on sample-gas parameters in wavelength-modulation spectroscopy for precise absorption measurements", Applied Physics B, Springer Berlin Heidelberg, Berlin/Heidelberg, vol. 67, Jan. 2, 1998, pp. 517-523, XP007921671, ISSN:0946-2171, DOI: 10.1007/ S003400050537.

Adame J A et al: "Application of cluster analysis to surface ozone, NOand SOdaily patterns in an industrial area in Central-Southern Spain measured with a DOAS system", Science of the Total Environment, Elsevier, Amsterdam, NL, vol. 429, Apr. 11, 2012 (Apr. 11, 2012), pp. 281-291, XP028491183, ISSN: 0048-9697, DOI: 10.1016/J.SCITOTENV.2012.04.032.

\* cited by examiner

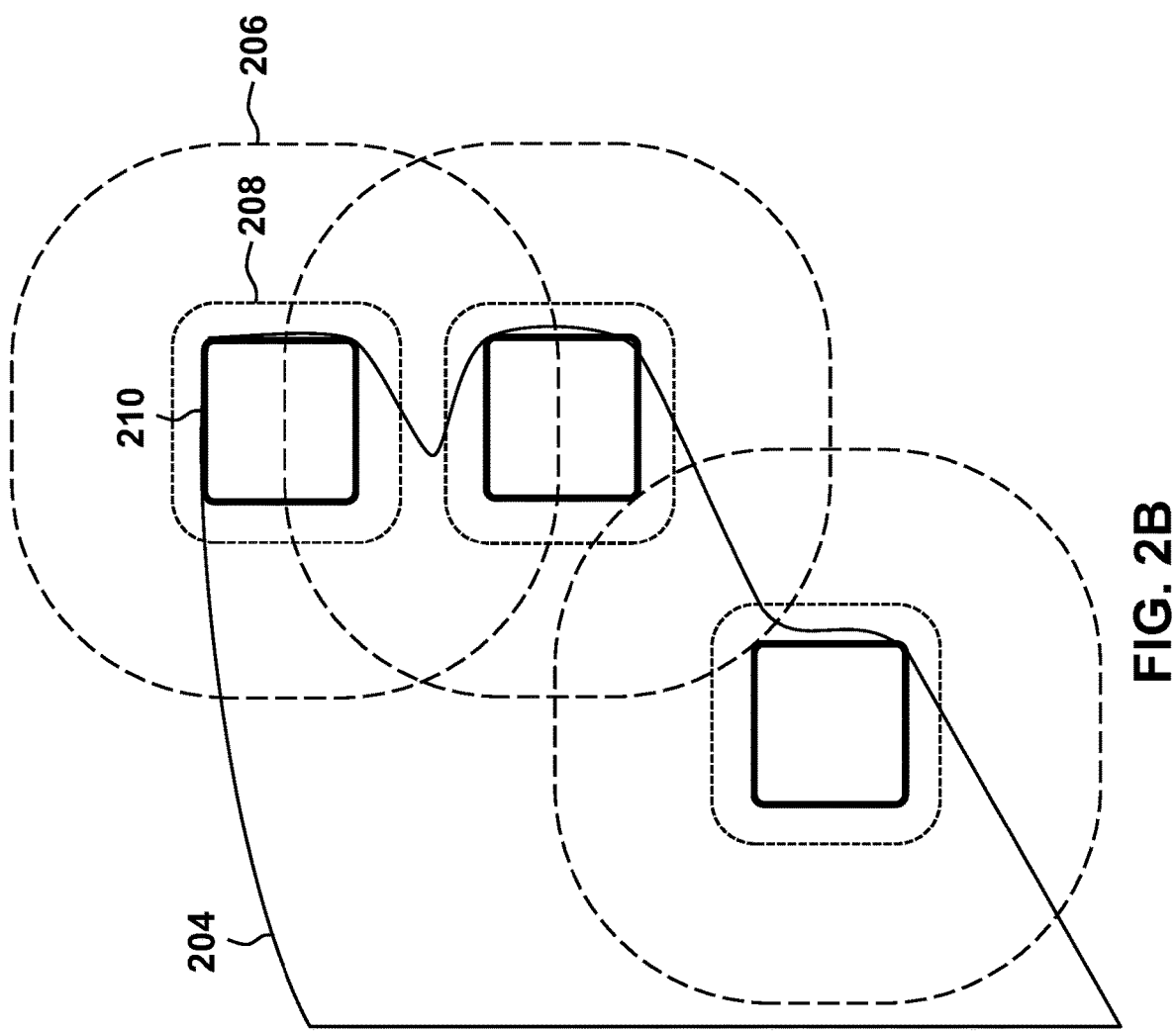

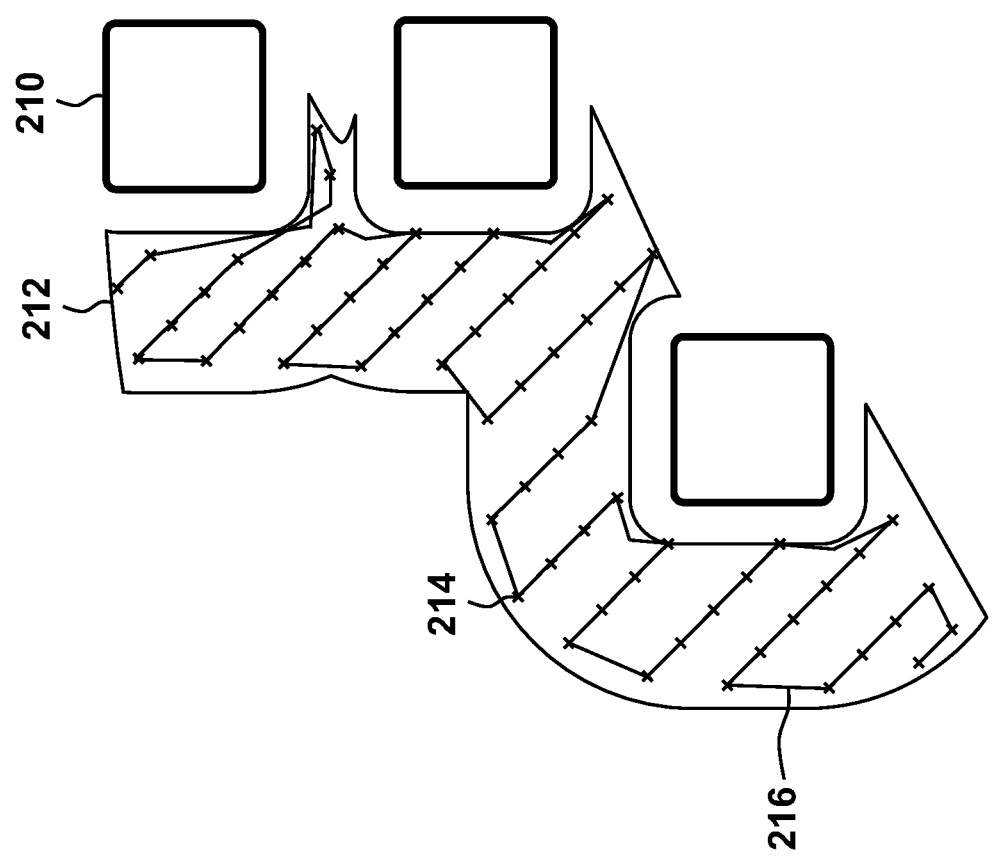

TIME-AND DATA-EFFICIENT ASSURANCE OF LEAK DETECTION

CROSS-REFERENCE TO RELATED APPLICATION

This application is a 35 U.S.C § 371 National Stage Entry of International Application No. PCT/US2020/026232, filed Apr. 1, 2020, which claims the priority benefit of U.S. Provisional Patent Application Ser. No. 62/829,752 filed Apr. 5, 2019, all of which are incorporated herein by reference in their entirety for all purposes.

FIELD OF ENDEAVOR

The invention relates to gas sensors, and more particularly to gas leak detection.

BACKGROUND

Trace gas sensors are used to detect and quantify leaks of toxic gases, e.g., hydrogen disulfide, or environmentally damaging gases, e.g., methane and sulfur dioxide, in a variety of industrial and environmental contexts. Detection and quantification of these leaks are of interest to a variety of industrial operations, e.g., oil and gas, chemical production, and painting, as well as environmental regulators for assessing compliance and mitigating environmental and safety risks.

SUMMARY

A system embodiment may include: an aerial vehicle; at least one trace-gas sensor disposed on the aerial vehicle, the trace-gas sensor configured to generate gas data; a global positioning system disposed on the aerial vehicle to determine a location of the at least one trace-gas sensor; and a processor having addressable memory, the processor configured to: receive a spatial location having one or more potential gas sources; receive a spatial location of the one or more potential gas sources; receive a desired level of confidence for detecting gas leaks from the one or more potential gas sources; receive a wind data for the received spatial location; determine a flight envelope encompassing one or more potential plume envelopes based on the received spatial location, the received spatial location of the one or more potential gas sources, the received desired level of confidence, and the received wind data; determine a flight path for the aerial vehicle, where the flight path covers a portion of the determined flight envelope; receive the gas data from the one or more gas trace-gas sensors of the portion of the determined flight envelope; and determine based on the received gas data whether a gas leak may be present in the received spatial location to the received desired level of confidence.

In additional system embodiments, the wind data may include a wind direction and a wind speed. In additional system embodiments, the wind data may include at least one of: a predicted wind direction and a predicted wind speed. In additional system embodiments, the portion of the determined flight envelope excludes a restricted zone, where the restricted zone may be an area within a set distance of each of the one or more potential gas sources.

In additional system embodiments, the at least one trace-gas sensor may be configured to detect hydrogen disulfide. In additional system embodiments, the at least one trace-gas sensor may be configured to detect methane. In additional system embodiments, the at least one trace-gas sensor may be configured to detect sulfur oxide. In additional system embodiments, the at least one trace-gas sensor may be configured to detect carbon dioxide. In additional system embodiments, the at least one trace-gas sensor may be configured to detect nitrogen oxide.

In additional system embodiments, the aerial vehicle may be an unmanned aerial vehicle (UAV). In additional system embodiments, the determined flight plan may include one or more random points within the determined one or more potential plume envelopes. In additional system embodiments, the one or more random points may be connected into a flight pattern using a route planning algorithm. In additional system embodiments, the route planning algorithm may be a traveling salesman algorithm.

A method embodiment may include: receiving, by a processor having addressable memory, a spatial location having one or more potential gas sources; receiving, by the processor, a spatial location of the one or more potential gas sources; receiving, by the processor, a desired level of confidence for detecting gas leaks from the one or more potential gas sources; receiving, by the processor, a wind data for the received spatial location; determining, by the processor, a flight envelope encompassing one or more potential plume envelopes based on the received spatial location, the received spatial location of the one or more potential gas sources, the received desired level of confidence, and the received wind data; determining, by the processor, a flight path for an aerial vehicle having at least one trace-gas sensor, where the flight path covers a portion of the determined flight envelope; receiving, by the processor, gas data from the one or more trace-gas sensors of the portion of the determined flight envelope; and determining, by the processor, based on the received gas data whether a gas leak may be present in the received spatial location to the received desired level of confidence.

Additional method embodiments may include: receiving, by the processor, a state of the one or more potential gas sources. In additional method embodiments, the at least one trace-gas sensor may be configured to detect at least one of: hydrogen disulfide, methane, sulfur oxide, carbon dioxide, and nitrogen oxide.

An additional system embodiment may include: a portable device; at least one trace-gas sensor disposed on the portable device, the trace-gas sensor configured to generate gas data; a global positioning system disposed on the portable device to determine a location of the at least one trace-gas sensor; and a processor having addressable memory, the processor configured to: receive a spatial location having one or more potential gas sources; receive a spatial location of the one or more potential gas sources; receive a desired level of confidence for detecting gas leaks from the one or more potential gas sources; receive a wind data for the received spatial location; determine a flight envelope encompassing one or more potential plume envelopes based on the received spatial location, the received spatial location of the one or more potential gas sources, the received desired level of confidence, and the received wind data; determine a path for the portable device, where the path covers a portion of the determined flight envelope; receive the gas data from the one or more gas trace-sensors of the portion of the determined flight envelope; and determine based on the received gas data whether a gas leak may be present in the received spatial location to the received desired level of confidence.

In additional system embodiments, the wind data comprises at least one of: a wind direction, a wind speed, a predicted wind direction, and a predicted wind speed. In additional system embodiments, the at least one trace-gas sensor may be configured to detect at least one of: hydrogen disulfide, methane, sulfur oxide, carbon dioxide, and nitrogen oxide. In additional system embodiments, the portion of the determined flight envelope excludes a restricted zone, where the restricted zone may be an area within a set distance of each of the one or more potential gas sources.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 2B depicts a close-up view of a portion of the plume envelope of FIG. 2A, according to one embodiment;

FIG. 2E depicts a flight path for the waypoints in the portion of the plume envelope of FIG. 2D, according to one embodiment;

DETAILED DESCRIPTION

Figure 1:
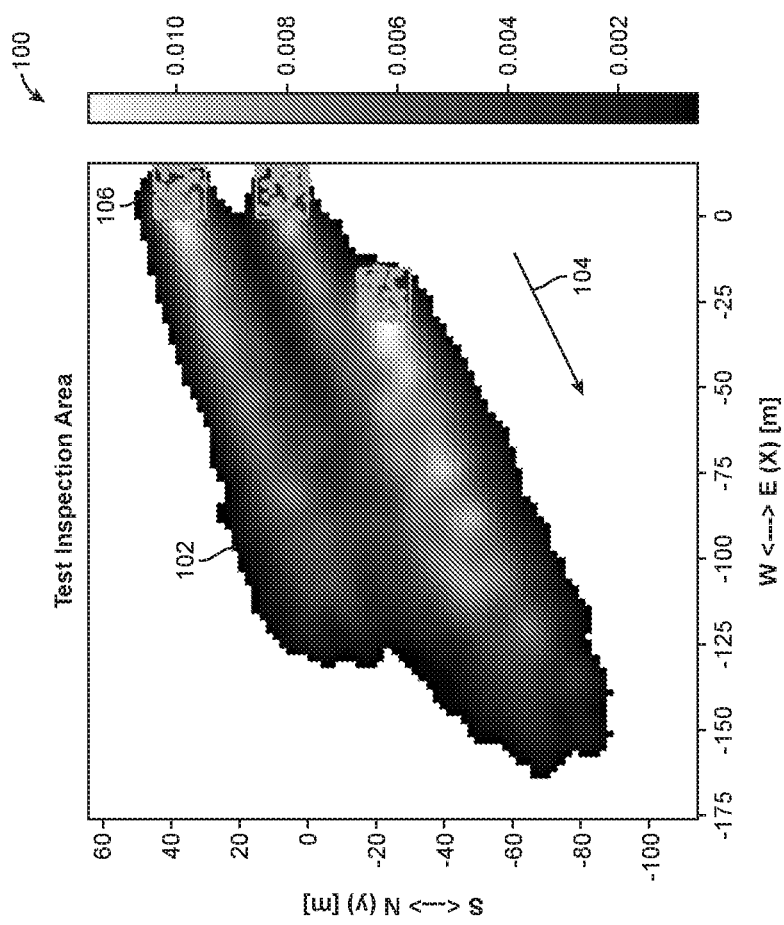
FIG. 1 depicts a forward model potential plume envelopes generated using wind data, according to one embodiment.

The following description is made for the purpose of illustrating the general principles of the embodiments discloses herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system allows for the creation of a flight plan to ascertain whether any gas leaks are present within a set spatial location. The spatial location may be a two-dimensional area, a three-dimensional area, a GPS location, and/or a geographical area. The created flight plan accounts for wind and a likelihood of the presence of gas leaks. This created flight plan allows for the determination, within a desired confidence level, as to whether any gas leaks are present in the set spatial location. This created flight plan may be accomplished by an aerial vehicle, such as an unmanned aerial vehicle, within a set time so as to provide time-efficient and data-efficient sampling of the set spatial location.

Trace gas sensors are used to detect and quantify leaks of toxic gases, e.g., hydrogen disulfide, or environmentally damaging gases, e.g., methane and sulfur dioxide, in a variety of industrial and environmental contexts. Detection and quantification of these leaks are of interest to a variety of industrial operations, e.g., oil and gas, chemical production, and painting, as well as environmental regulators for assessing compliance and mitigating environmental and safety risks.

The recent availability of small, highly maneuverable, remotely piloted airborne platforms presents an opportunity to detect, localize, and quantify leaks at industrial sites. The presence of a leak can be ascertained by flying downwind of a site and surveying for the gas of interest. If the gas of interest is detected, the leak location and quantification can be determined by subsequent surveys, each moving upstream until the source of the leak is determined.

In practice, leak localization and detection are made more challenging by the dynamic nature of wind and the limited flight duration of aerial platforms. For example, if no trace gas is detected downwind of a site, without taking into account the details of local weather patterns, there is no a prioi guarantee of no leaks at that site given that winds are constantly changing direction and velocity. For example, the trace gas may have been blowing in a direction that the survey did not capture. For a leak detection method to be effective, site operators and regulators may require assurances that a site is leak free with a high confidence, i.e., site operators and regulators aim to minimize the likelihood of a false negative.

While it is possible to fly a route that reduces the likelihood of missing the discovery of a leak within a survey area, flying such a flight pattern downwind of an industrial site requires expert knowledge of dynamic jet propagation and mixing. It would be an advance in the art to provide flight platform operators an envelope and route to follow that time- and space-efficiently surveys a site and can determine, with a computed level of confidence, whether the site is leak free.

This advance in the art is achieved by fusing local wind measurements with flight planning and operation. By measuring and recording local wind data and making intelligent assumptions about leak sources based on equipment located on site, a flight envelope can be computed using a physics-based forward-computed fluid mixing model. This forward-model takes in a time series of point measurements of wind speed, direction, and variance, and, based on conservation of fluid momentum and mass, computes the probability that the gas of interest will be present at any given time in each discretized location in the survey area.

Then, once flight envelopes are computed, flight trajectories may be computed to efficiently sample this space, by maximizing the flight space covered in the shortest amount of time, while simultaneously maximizing the confidence level of a leak false negative.

FIG. 1 depicts a forward model 100 potential plume envelopes 102 generated using wind 104 data, according to one embodiment. Wind 104 creates potential plume envelopes 102 from potential gas sources 106. Each potential gas source 106 may be a single potential gas source or a cluster of potential gas sources.

Figure 2A:
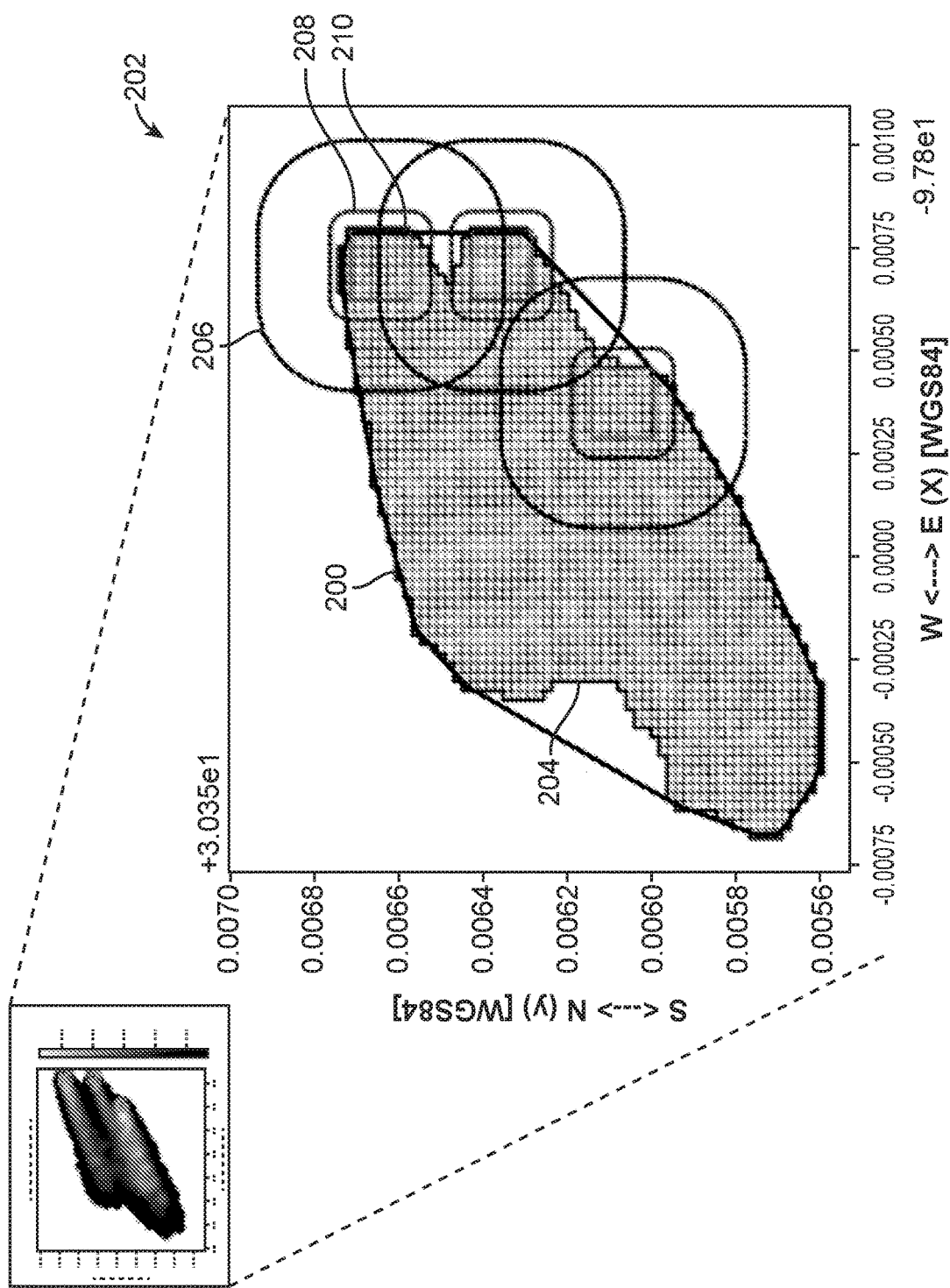
FIG. 2A depicts a flight envelope calculated from forward model plume mixing, according to one embodiment.

FIG. 2A depicts a flight envelope 200 calculated from forward model plume mixing 202, according to one embodiment. The flight envelope 200 encompasses the potential plume envelopes 204, as shown in FIG. 1 as 102. The plume envelopes 204 may be a two-dimensional location in some embodiments. In other embodiments, the plume envelopes 204 may be a three-dimensional area. The plume envelopes 204 may account for rising or falling gases based on the wind direction, wind speed, type of gas from each potential gas source 210, and the like. Each of the one or more potential gas sources 210 may each have an associated restricted zone 208. The restricted zone may be a no-fly, or no entry, area within a set distance of a potential gas source 210. The restricted zone 210 may be based on user preference, regulations, and/or type of potential gas source 210. For example, some potential gas sources 210 may have larger restricted zones 210 than other potential gas sources 210. The optimal flight area 206 for each potential gas source 210 is based on the desired confidence level for detecting a gas leak. The optimal flight area 206 may be expanded for an increased desired confidence level. The optimal flight area 206 may be reduced for a decreased desired confidence level. In some embodiments, the optimal flight area 206 may be increased for higher winds and decreased for lower winds.

FIG. 2B depicts a close-up view of a portion of the plume envelope 204 of FIG. 2A, according to one embodiment. As shown in FIG. 2B, only a portion of the optimal flight area 206 surrounding each potential gas source 210 overlaps with the potential plume envelope 204 due to the wind direction and wind speed.

Figure 2C:
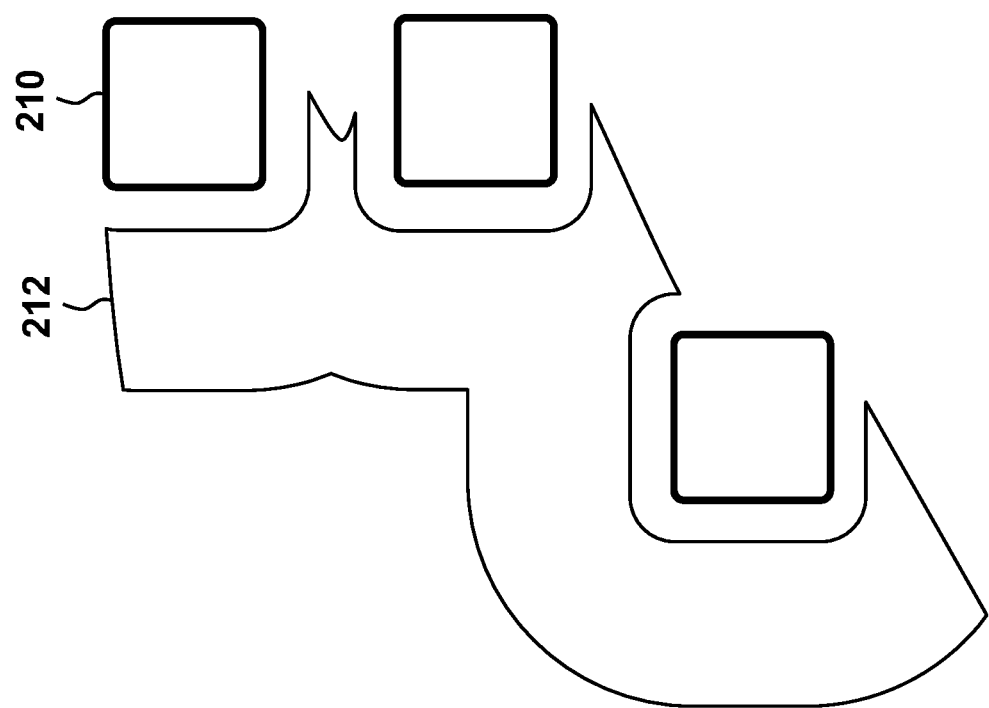
FIG. 2C depicts a portion of the plume envelope of FIG. 2B to be sampled, according to one embodiment.

FIG. 2C depicts a portion 212 of the plume envelope of FIG. 2B to be sampled, according to one embodiment. The overlapping area between the optimal flight area 206, as shown in FIG. 2B, and the potential plume envelope 204, as shown in FIG. 2B, is the portion 212 of the plume envelope to be sampled. This portion 212 of the plume envelope includes the areas likely to include trace-gas if a gas leak is present while excluding any restricted zones 208, as shown in FIG. 2B, around each possible gas source 210.

Figure 2D:
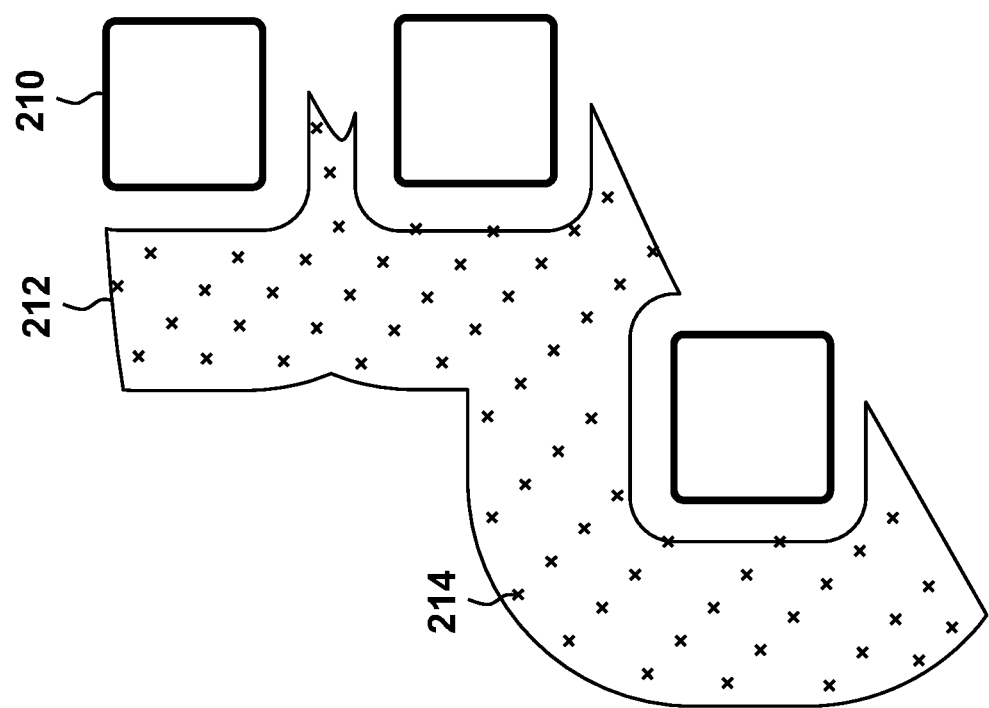
FIG. 2D depicts waypoints in the portion of the plume envelope of FIG. 2C to be sampled, according to one embodiment.

FIG. 2D depicts waypoints 214 in the portion 212 of the plume envelope of FIG. 2C to be sampled, according to one embodiment. One or more waypoints 214 may be added in the portion 212 of the plume envelope to be sampled. The waypoints 214 may be distributed in a uniform, random, or other pattern. In some embodiments, waypoints 214 may be positioned in a greater density closer to each potential gas source 210. The waypoints 214 may be positioned in a lower density farther away from each potential gas source 210. The number and/or location of the waypoints 214 may be based on the desired level of confidence for detecting any gas leaks for the potential gas sources 210.

Figure 3:
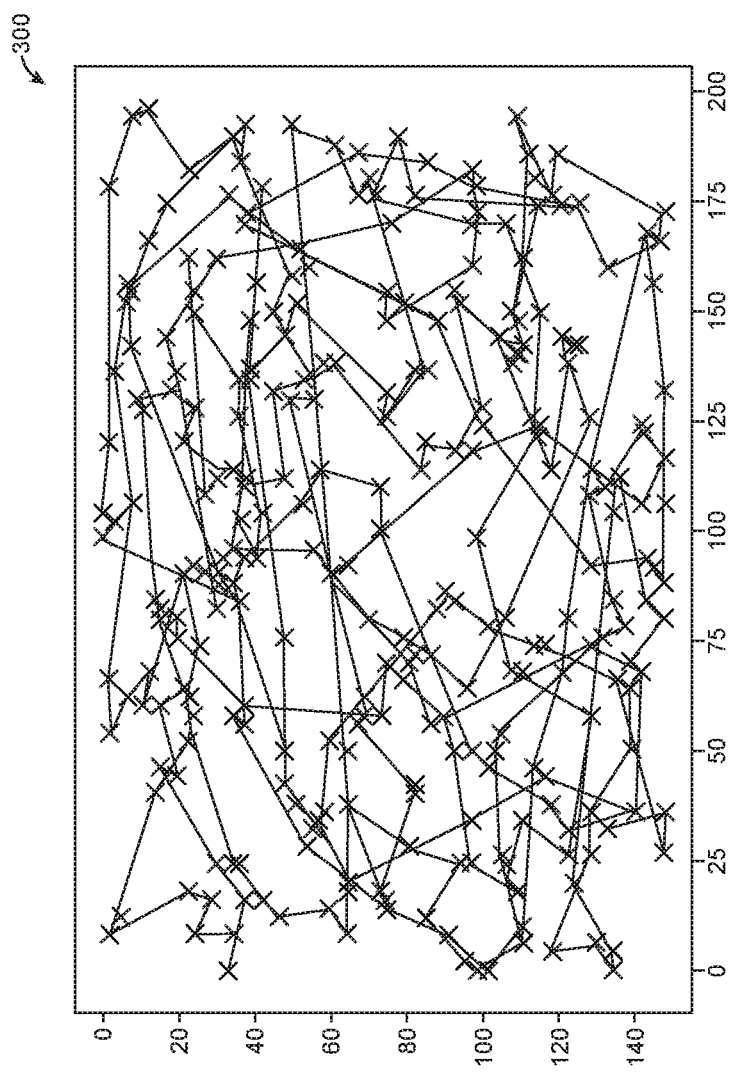
FIG. 3 depicts random waypoints with a traveling salesman route, according to one embodiment.

FIG. 2E depicts a flight path 216 for the waypoints 214 in the portion 212 of the plume envelope of FIG. 2D, according to one embodiment. A raster pattern may be used as the flight path 216 to connect the waypoints 214. In other embodiments, a traveling salesman route, as shown in FIG. 3, or other route may be used to connect the waypoints 214 within the portion 212 of the plume envelope. The flight path may be contained within the portion 210 of the plume envelope. In other embodiments, the flight path may avoid going into the restricted zone 208, as shown in FIG. 2B. In one embodiment, the flight path may be a random walk to connect waypoints 214. While waypoints are shown, the flight path 216 may be generated by the system and method disclosed herein so as to cover the portion 212 of the plume envelope to be sampled at the desired level of confidence for detecting trace-gas leaks from the potential gas sources 210.

FIG. 3 depicts random waypoints 300 with a traveling salesman route, according to one embodiment. In some embodiments, the start point and finish point may be different. One method for efficiently traversing the flight envelope is to randomly disperse waypoints across the plume, as shown in FIG. 1, and/or the flight envelope, as shown in FIG. 2, in densities proportional to likelihood of gas being present within the flight envelope. These random points are then connected into a flight pattern using a route planning algorithm, such as the traveling salesman algorithm. The resulting data is reconstructed into a 3D representation of the space using an L1-norm regression and an appropriate basis set, e.g., a wavelet or discrete cosine transform.

This approach disclosed herein yields relatively narrow flight windows for low-variance wind conditions, and it yields larger flight envelopes for high-variance wind conditions. The random distribution of flight waypoints forces the sensor to spend more time sampling regions with a high likelihood of gas and eliminates any sampling bias introduced by rastering.

Furthermore, in a post-processing step, a given site that has been deemed free of leaks after flying a known flight path can be simulated in a Monte Carlo fashion, using the same walk-forward model described above, testing the assumptions put in place regarding potential leak sources, and quantifying the level of confidence that a site is, indeed, free of any leaks. In some embodiments, a Monte Carlo simulation, or other simulation, may be used to determine the one or more potential plume envelopes.

Figure 4A:
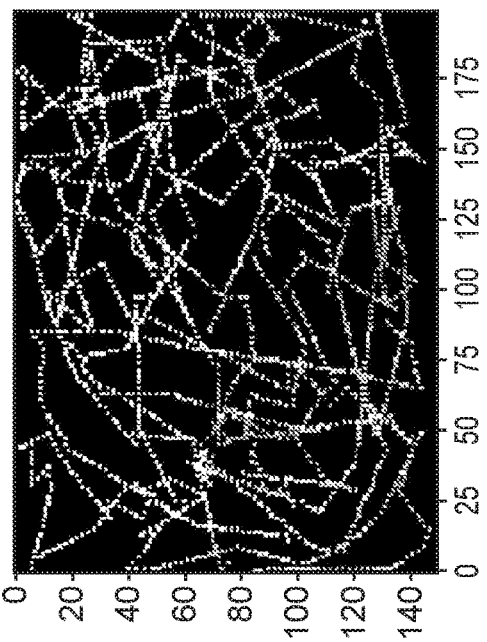
FIG. 4A depicts an image of an area to be sampled, according to one embodiment.

FIG. 4A depicts an image of an area to be sampled 402, according to one embodiment.

Figure 4B:
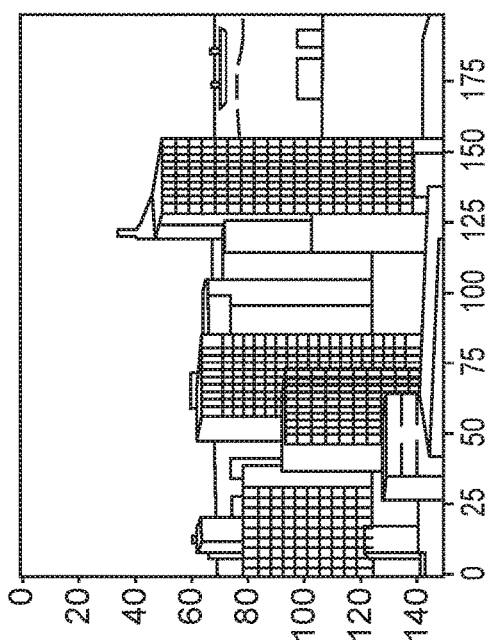
FIG. 4B depicts random samples of the image of FIG. 4A along the paths traversed in FIG. 2, according to one embodiment.

FIG. 4B depicts random samples 404 of the image of FIG. 4A along the paths traversed in FIG. 2, according to one embodiment.

Figure 4C:
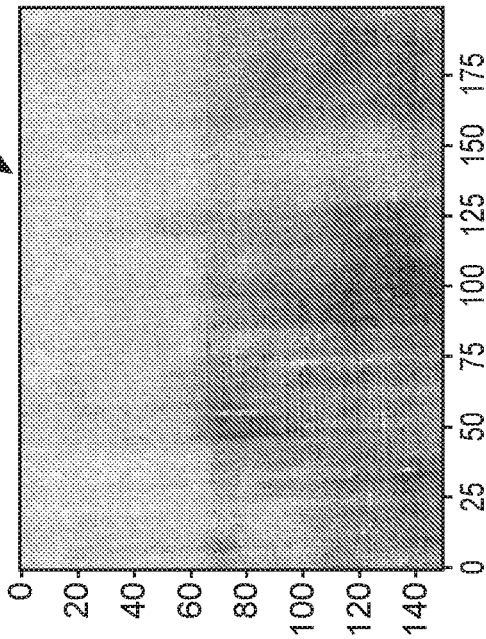
FIG. 4C depicts a reconstructed image from the random samples of FIG. 4B, according to one embodiment.

FIG. 4C depicts a reconstructed image 406 from the random samples of FIG. 4B, according to one embodiment.

Figure 5:
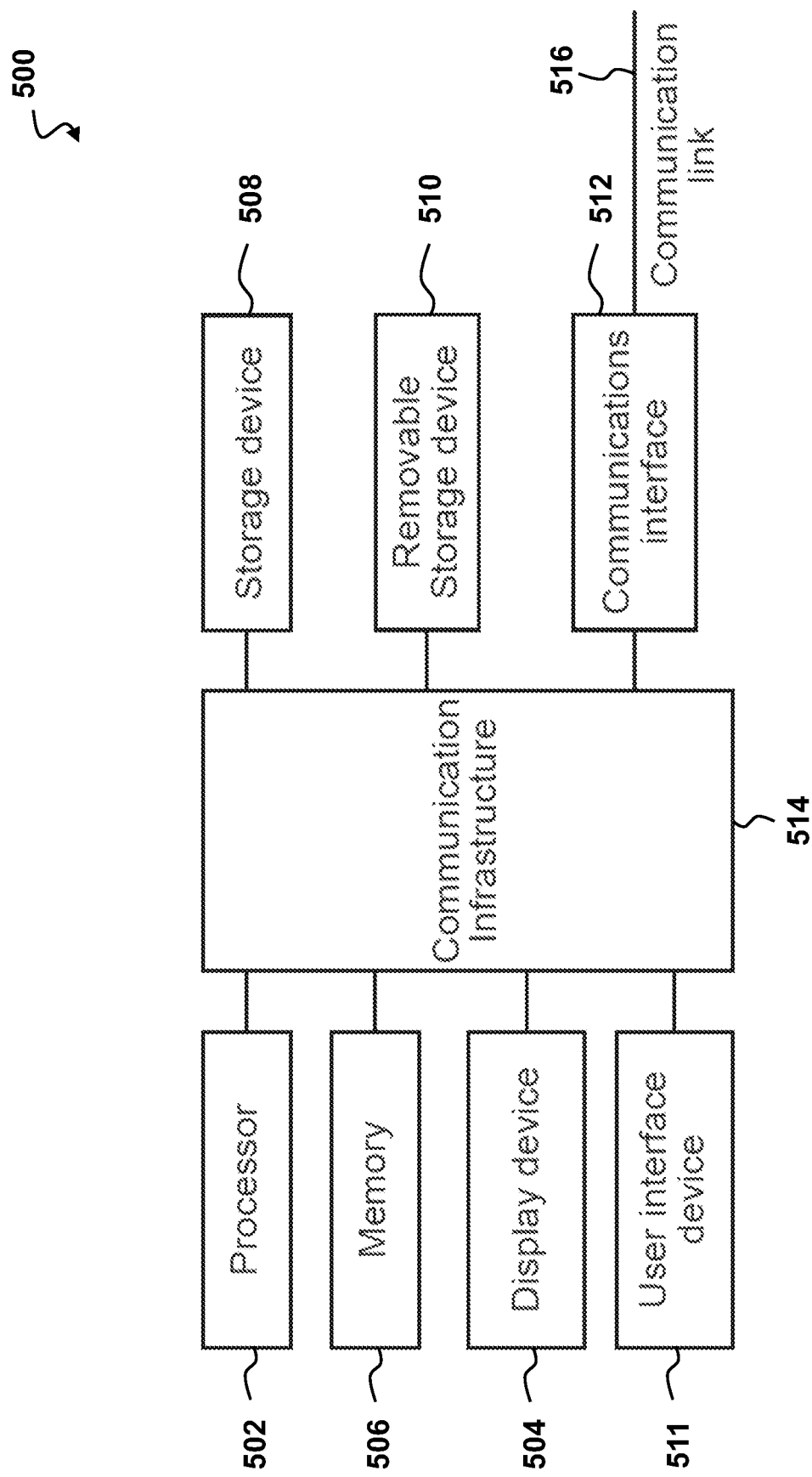
FIG. 5 shows a high-level block diagram and process of a computing system for implementing an embodiment of the system and process.

FIG. 5 is a high-level block diagram 500 showing a computing system comprising a computer system useful for implementing an embodiment of the system and process, disclosed herein. Embodiments of the system may be implemented in different computing environments. The computer system includes one or more processors 502, and can further include an electronic display device 504 (e.g., for displaying graphics, text, and other data), a main memory 506 (e.g., random access memory (RAM)), storage device 508, a removable storage device 510 (e.g., removable storage drive, a removable memory module, a magnetic tape drive, an optical disk drive, a computer readable medium having stored therein computer software and/or data), user interface device 511 (e.g., keyboard, touch screen, keypad, pointing device), and a communication interface 512 (e.g., modem, a network interface (such as an Ethernet card), a communications port, or a PCMCIA slot and card). The communication interface 512 allows software and data to be transferred between the computer system and external devices.

The system further includes a communications infrastructure 514 (e.g., a communications bus, cross-over bar, or network) to which the aforementioned devices and modules are connected as shown.

Information transferred via communications interface 514 may be in the form of signals such as electronic, electromagnetic, optical, or other signals capable of being received by communications interface 514, via a communication link 516 that carries signals and may be implemented using wire or cable, fiber optics, a phone line, a cellular/mobile phone link, a radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 512. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 6:
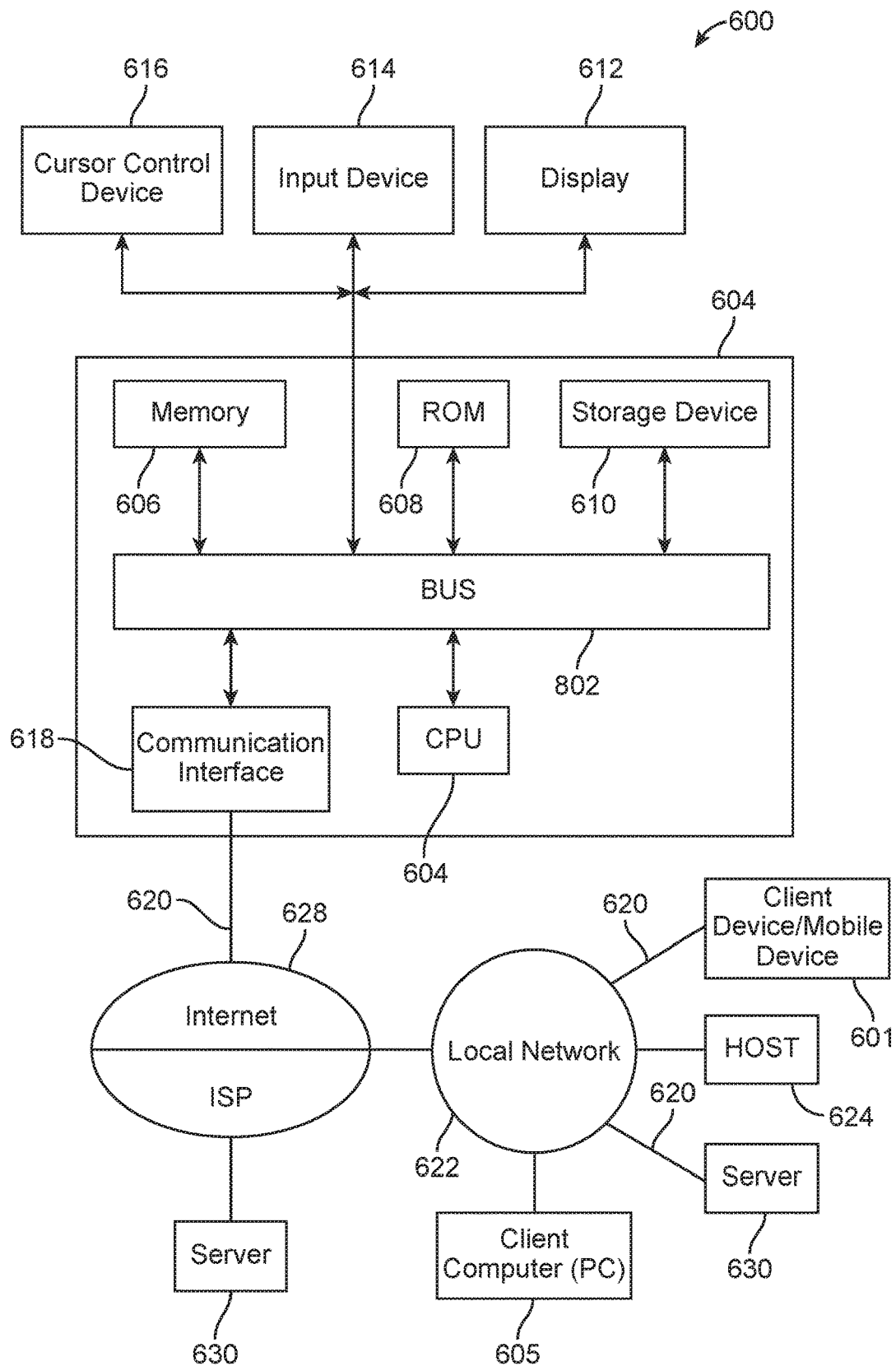
FIG. 6 shows a block diagram and process of an exemplary system in which an embodiment may be implemented.

FIG. 6 shows a block diagram of an example system 600 in which an embodiment may be implemented. The system 600 includes one or more client devices 601 such as consumer electronics devices, connected to one or more server computing systems 630. A server 630 includes a bus 602 or other communication mechanism for communicating information, and a processor (CPU) 604 coupled with the bus 602 for processing information. The server 630 also includes a main memory 606, such as a random access memory (RAM) or other dynamic storage device, coupled to the bus 602 for storing information and instructions to be executed by the processor 604. The main memory 606 also may be used for storing temporary variables or other intermediate information during execution or instructions to be executed by the processor 604. The server computer system 630 further includes a read only memory (ROM) 608 or other static storage device coupled to the bus 602 for storing static information and instructions for the processor 604. A storage device 610, such as a magnetic disk or optical disk, is provided and coupled to the bus 602 for storing information and instructions. The bus 602 may contain, for example, thirty-two address lines for addressing video memory or main memory 606. The bus 602 can also include, for example, a 32-bit data bus for transferring data between and among the components, such as the CPU 604, the main memory 606, video memory and the storage 610. Alternatively, multiplex data/address lines may be used instead of separate data and address lines.

The server 630 may be coupled via the bus 602 to a display 612 for displaying information to a computer user. An input device 614, including alphanumeric and other keys, is coupled to the bus 602 for communicating information and command selections to the processor 604. Another type or user input device comprises cursor control 616, such as a mouse, a trackball, or cursor direction keys for communicating direction information and command selections to the processor 604 and for controlling cursor movement on the display 612.

According to one embodiment, the functions are performed by the processor 604 executing one or more sequences of one or more instructions contained in the main memory 606. Such instructions may be read into the main memory 606 from another computer-readable medium, such as the storage device 610. Execution of the sequences of instructions contained in the main memory 606 causes the processor 604 to perform the process steps described herein. One or more processors in a multi-processing arrangement may also be employed to execute the sequences of instructions contained in the main memory 606. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 604 for execution. Such a medium may take many forms, including but not limited to, non-volatile media, volatile media, and transmission media. Non-volatile media includes, for example, optical or magnetic disks, such as the storage device 610. Volatile media includes dynamic memory, such as the main memory 606. Transmission media includes coaxial cables, copper wire and fiber optics, including the wires that comprise the bus 602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 604 for execution. For example, the instructions may initially be carried on a magnetic disk of a remote computer. The remote computer can load the instructions into its dynamic memory and send the instructions over a telephone line using a modem. A modem local to the server 630 can receive the data on the telephone line and use an infrared transmitter to convert the data to an infrared signal. An infrared detector coupled to the bus 602 can receive the data carried in the infrared signal and place the data on the bus 602. The bus 602 carries the data to the main memory 606, from which the processor 604 retrieves and executes the instructions. The instructions received from the main memory 606 may optionally be stored on the storage device 610 either before or after execution by the processor 604.

The server 630 also includes a communication interface 618 coupled to the bus 602. The communication interface 618 provides a two-way data communication coupling to a network link 620 that is connected to the world wide packet data communication network now commonly referred to as the Internet 628. The Internet 628 uses electrical, electromagnetic or optical signals that carry digital data streams. The signals through the various networks and the signals on the network link 620 and through the communication interface 618, which carry the digital data to and from the server 630, are exemplary forms or carrier waves transporting the information.

In another embodiment of the server 630, interface 618 is connected to a network 622 via a communication link 620. For example, the communication interface 618 may be an integrated services digital network (ISDN) card or a modem to provide a data communication connection to a corresponding type of telephone line, which can comprise part of the network link 620. As another example, the communication interface 618 may be a local area network (LAN) card to provide a data communication connection to a compatible LAN. Wireless links may also be implemented. In any such implementation, the communication interface 618 sends and receives electrical electromagnetic or optical signals that carry digital data streams representing various types of information.

The network link 620 typically provides data communication through one or more networks to other data devices. For example, the network link 620 may provide a connection through the local network 622 to a host computer 624 or to data equipment operated by an Internet Service Provider (ISP). The ISP in turn provides data communication services through the Internet 628. The local network 622 and the Internet 628 both use electrical, electromagnetic or optical signals that carry digital data streams. The signals through the various networks and the signals on the network link 620 and through the communication interface 618, which carry the digital data to and from the server 630, are exemplary forms or carrier waves transporting the information.

The server 630 can send/receive messages and data, including e-mail, program code, through the network, the network link 620 and the communication interface 618. Further, the communication interface 618 can comprise a USB/Tuner and the network link 620 may be an antenna or cable for connecting the server 630 to a cable provider, satellite provider or other terrestrial transmission system for receiving messages, data and program code from another source.

The example versions of the embodiments described herein may be implemented as logical operations in a distributed processing system such as the system 600 including the servers 630. The logical operations of the embodiments may be implemented as a sequence of steps executing in the server 630, and as interconnected machine modules within the system 600. The implementation is a matter of choice and can depend on performance of the system 600 implementing the embodiments. As such, the logical operations constituting said example versions of the embodiments are referred to for e.g., as operations, steps or modules.

Similar to a server 630 described above, a client device 601 can include a processor, memory, storage device, display, input device and communication interface (e.g., e-mail interface) for connecting the client device to the Internet 628, the ISP, or LAN 622, for communication with the servers 630.

The system 600 can further include computers (e.g., personal computers, computing nodes) 605 operating in the same manner as client devices 601, wherein a user can utilize one or more computers 605 to manage data in the server 630.

Figure 7:
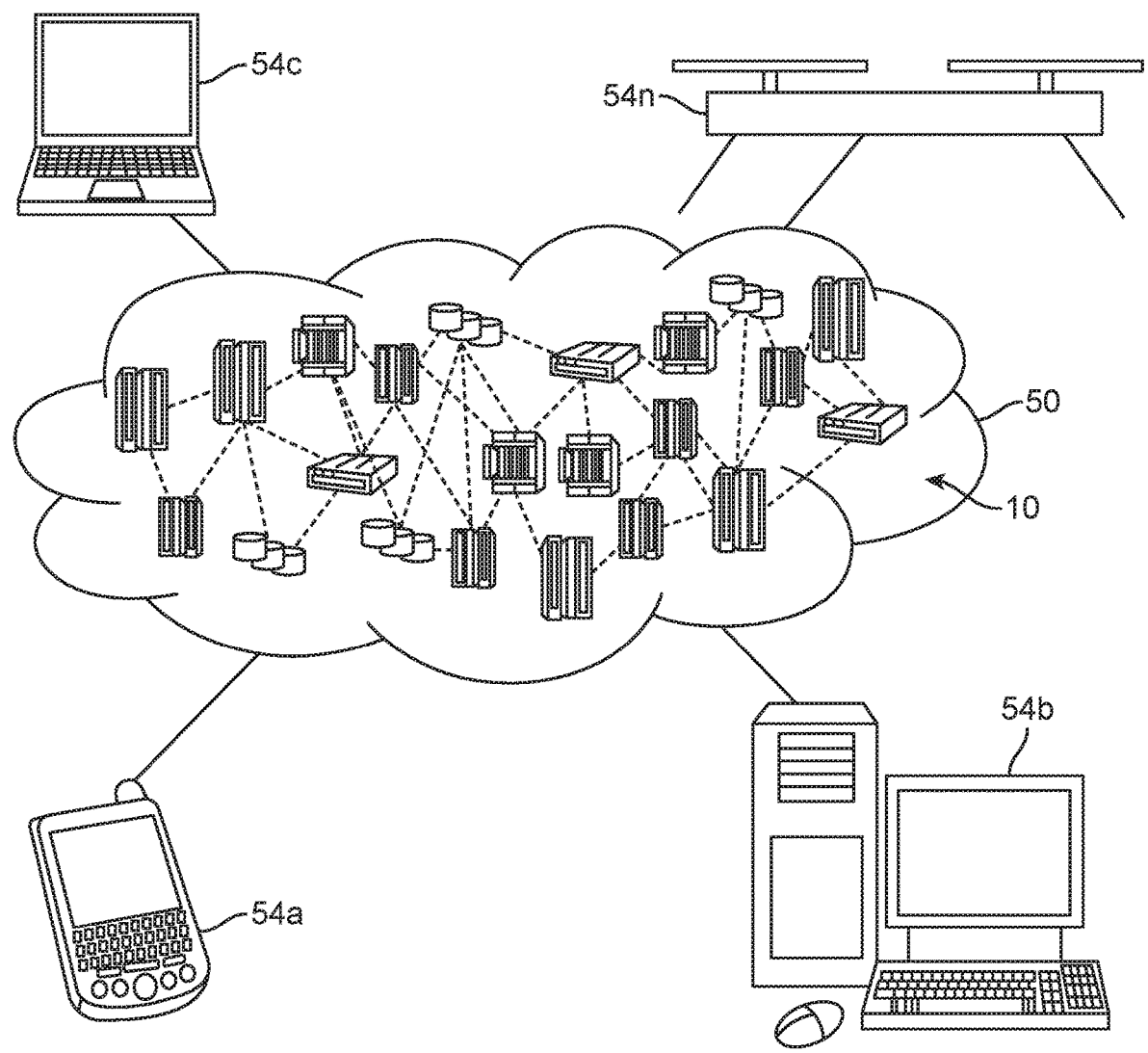
FIG. 7 depicts a cloud computing environment for implementing an embodiment of the system and process disclosed herein.

Referring now to FIG. 7, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or UAV 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8A:
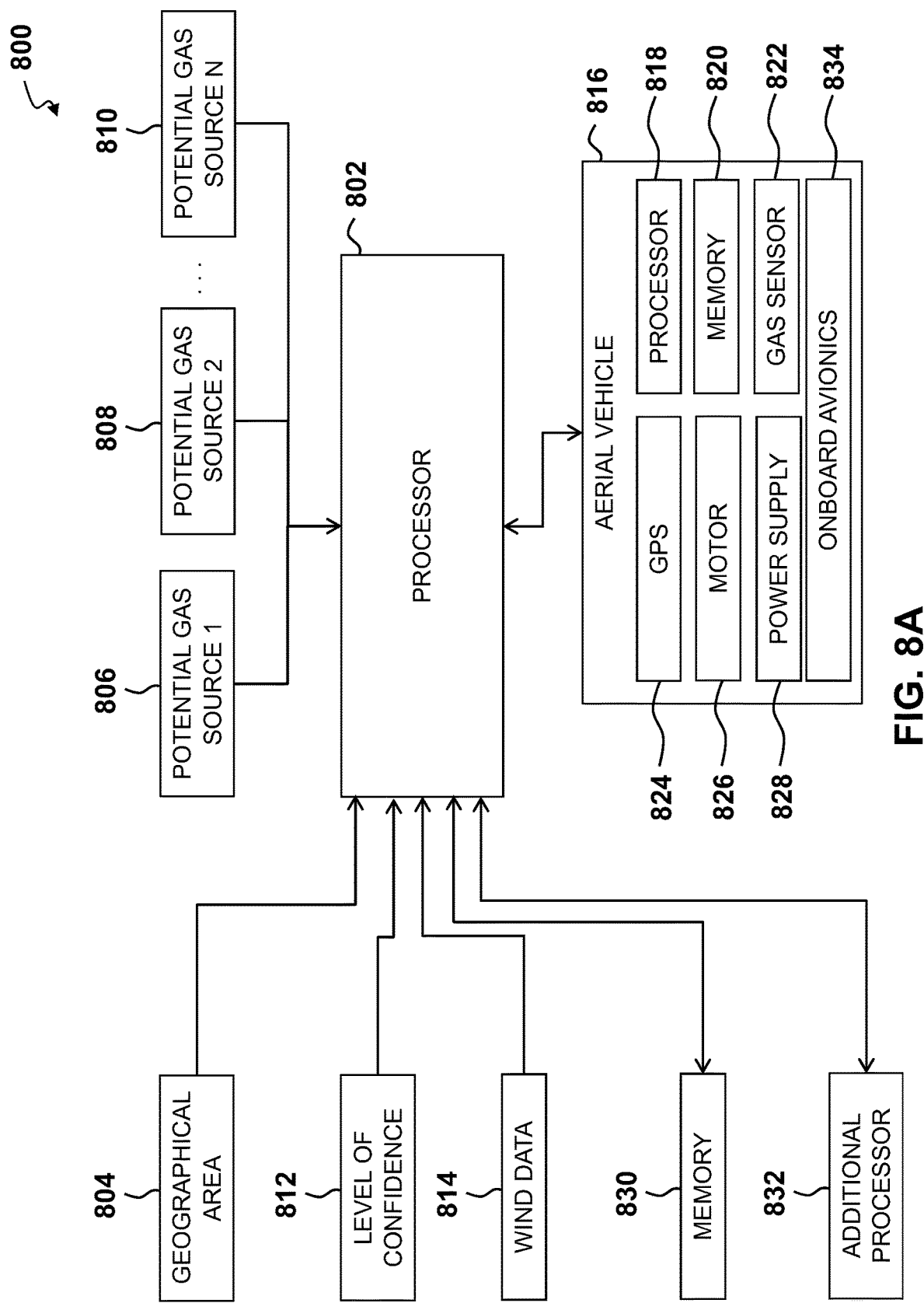
FIG. 8A depicts a high-level block diagram of a gas leak detection system, according to one embodiment.

FIG. 8A depicts a high-level block diagram of a gas leak detection system 800, according to one embodiment. The system includes a processor 802. The processor 802 receives a spatial location 804, which may be an area containing one or more potential gas sources 806, 808, 810. The processor 802 receives the spatial location of the one or more potential gas sources 806, 808, 810 within the spatial location 804. The one or more potential gas sources 806, 808, 810 may be equipment and/or locations more likely to leak toxic gases, such as hydrogen disulfide, or environmentally damaging gases, such as methane and sulfur dioxide. In some embodiments, the at least one gas sensor 822 may be configured to detect carbon dioxide. In other embodiments, the at least one gas sensor 822 may be configured to detect nitrogen oxide. In other embodiments, the at least one gas sensor 822 may be configured to detect sulfur oxide, such as SO, $SO_2$, $SO_3$, $S_7O_2$, $S_6O_2$, $S_2O_2$, and the like. The processor 802 may also receive a level of confidence 812 desired as to whether any gas leaks are present within the received spatial location 804. The higher the level of confidence 812, the longer it may take the system 800 to determine whether any gas leaks are present in the spatial location 804. A reasonably high level of confidence 812 may be achieved in a time-efficient manner using the system 800 disclosed herein. The processor 802 may also receive wind data 814. Wind data 814 may include wind speed and/or wind direction for the spatial location 804. In some embodiments, wind data 814 may also include predictions as to changes in the wind speed and/or wind direction.

The processor 802 may determine one or more potential plume envelopes, such as shown in FIG. 2. The potential plume envelopes cover potential plumes from gas leaks emanating from the one or more potential gas sources 806, 808, 810. The one or more potential plume envelopes contain the area that will be tested by one or more gas leak sensors.

The processor then determines a flight path for an aerial vehicle 816 having at least one gas sensor 822. The flight path for the aerial vehicle 816 covers the one or more potential plume envelopes determined by the processor 802. The aerial vehicle 816 may be an unmanned aerial vehicle (UAV) in some embodiments. The aerial vehicle 816 may have a processor 818 in communication with addressable memory 820, a GPS 824, one or more motors 826, and a power supply 828. The aerial vehicle 816 may receive the flight plan from the processor 802 and communicate gathered gas sensor 822 sensor to the processor 802. The GPS 824 may record the location of the aerial vehicle 816 when each gas sensor 822 data is acquired. The GPS 824 may also allow the aerial vehicle 816 to travel the flight path generated by the processor 802. In some embodiments, the location of the aerial vehicle 816 may be determined by an onboard avionics 834. The onboard avionics 834 may include a triangulation system, a beacon, a spatial coordinate system, or the like. The onboard avionics 834 may be used with the GPS 824 in some embodiments. In other embodiments, the aerial vehicle 816 may use only one of the GPS 824 and the onboard avionics 834.

The power supply 828 may be a battery in some embodiments. The power supply 828 may limit the available flight time for the aerial vehicle 816 and so it is crucial that the potential plume envelopes are accurate to allow for data that can be used to make a determination as to whether there are any gas leaks within the desired level of confidence 812. In some embodiments, the flight plan may be split up into two or more flights based on a size of the potential plumes, a flight time of the aerial vehicle 816, weather conditions, and the like. In some embodiments, the processor 802 may be a part of the aerial vehicle 816, a cloud computing device, a ground control station (GCS) used to control the aerial vehicle 816, or the like.

The processor 802 may receive gas data from the one or more gas sensors 822 of the aerial vehicle 816. The processor may then determine, based on the received gas data, whether a gas leak is present in the received spatial location to the desired level of confidence. If a gas leak is not detected, no immediate action is needed and further tests may be accomplished in the future to ensure that no gas leaks develop. If a gas leak is detected, then corrective action may be taken to minimize and/or stop the gas leak.

In some embodiments, the processor 802 may be in communication with addressable memory 830. The memory may store the result of whether a gas leak was detected, historical gas data, the received spatial location 804, potential gas sources 806, 808, 810, level of confidence 812, wind data 814, and/or aerial vehicle 816 information. In some embodiments, the processor 802 may be in communication with an additional processor 832. The additional processor 832 may be a part of the aerial vehicle 816, a cloud computing device, a GCS used to control the aerial vehicle 816, or the like.

Figure 8B:
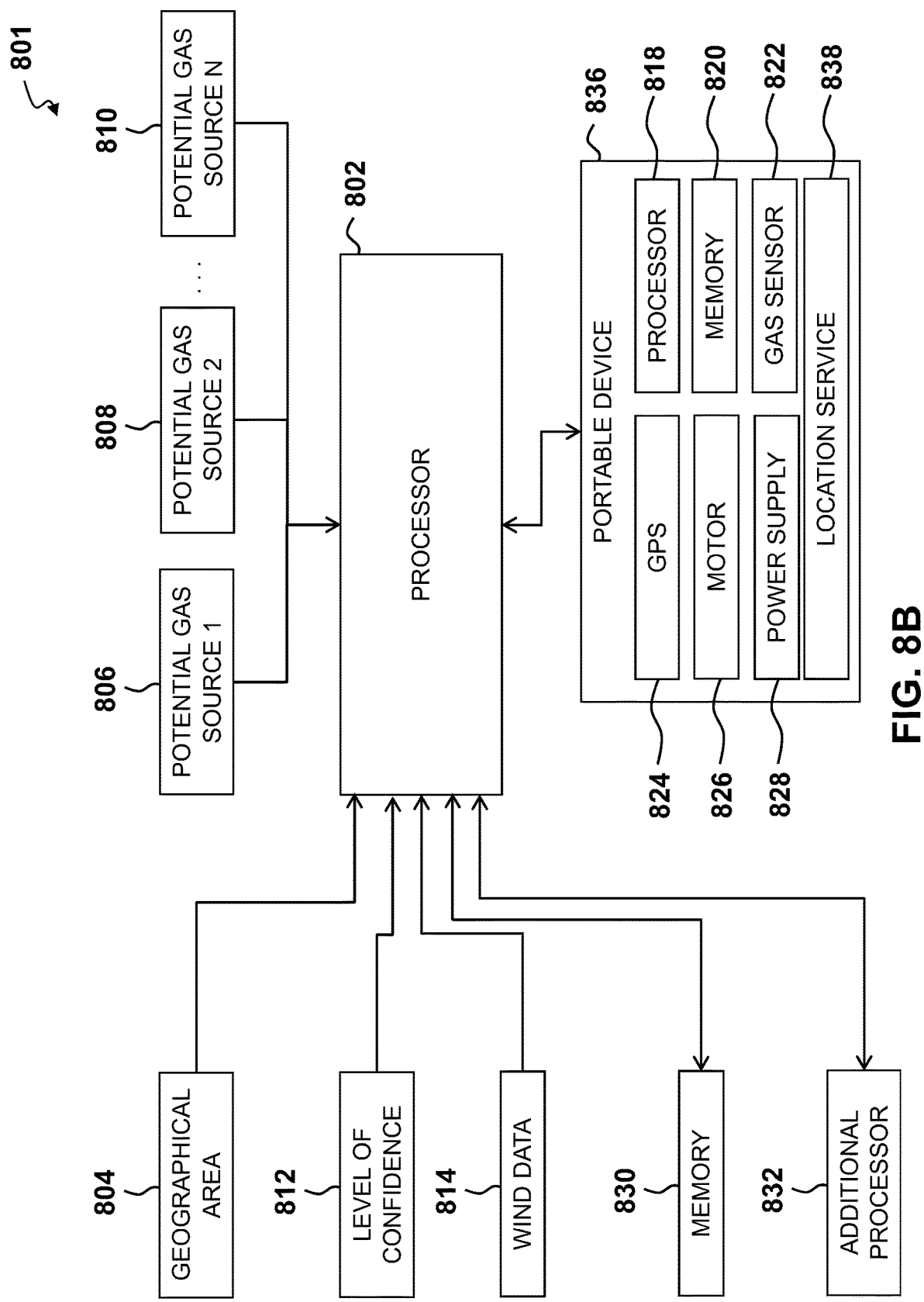
FIG. 8B depicts a high-level block diagram of an alternate gas leak detection system, according to one embodiment.

FIG. 8B depicts a high-level block diagram of an alternate gas leak detection system 801, according to one embodiment. The system includes a processor 802. The processor 802 receives a spatial location 804, which may be an area containing one or more potential gas sources 806, 808, 810. The processor 802 receives the spatial location of the one or more potential gas sources 806, 808, 810 within the spatial location 804. The one or more potential gas sources 806, 808, 810 may be equipment and/or locations more likely to leak toxic gases, such as hydrogen disulfide, or environmentally damaging gases, such as methane and sulfur dioxide. The processor 802 may also receive a level of confidence 812 desired as to whether any gas leaks are present within the received spatial location 804. The higher the level of confidence 812, the longer it may take the system 800 to determine whether any gas leaks are present in the spatial location 804. A reasonably high level of confidence 812 may be achieved in a time-efficient manner using the system 800 disclosed herein. The processor 802 may also receive wind data 814. Wind data 814 may include wind speed and/or wind direction for the spatial location 804. In some embodiments, wind data 814 may also include predictions as to changes in the wind speed and/or wind direction.

The processor 802 may determine one or more potential plume envelopes, such as shown in FIG. 2. The potential plume envelopes cover potential plumes from gas leaks emanating from the one or more potential gas sources 806, 808, 810. The one or more potential plume envelopes contain the area that will be tested by one or more gas leak sensors.

The processor then determines a path for a portable device 836 having at least one gas sensor 822. The portable device 836 may be a handheld device, a robot-mounted device, an aerial vehicle (AV), an unmanned aerial vehicle (UAV), or the like. The path for the portable device 836 covers the one or more potential plume envelopes determined by the processor 802. The portable device 836 may have a processor 818 in communication with addressable memory 820, a GPS 824, one or more motors 826, and a power supply 828. The portable device 836 may receive the path from the processor 802 and communicate gathered gas sensor 822 sensor data to the processor 802. The GPS 824 may record the location of the portable device 836 when each gas sensor 822 data is acquired. The GPS 824 may also allow the portable device 836 to travel the path generated by the processor 802. In some embodiments, the location of the portable device 836 may be determined by a location service 838. The location service 838 may include a triangulation system, a beacon, a spatial coordinate system, or the like. The location service 838 may be used with the GPS 824 in some embodiments. In other embodiments, the portable device 836 may use only one of the GPS 824 and the location service 838.

The power supply 828 may be a battery in some embodiments. The power supply 828 may limit the available data gathering time for the portable device 836 and so it is crucial that the potential plume envelopes are accurate to allow for data that can be used to make a determination as to whether there are any gas leaks within the desired level of confidence 812. In some embodiments, the path may be split up into two or more paths based on a size of the potential plumes, a path time of the portable device 836, weather conditions, and the like. In some embodiments, the processor 802 may be a part of the portable device 836, a cloud computing device, a controller used to control the portable device 836, or the like.

The processor 802 may receive gas data from the one or more gas sensors 822 of the portable device 836. The processor may then determine, based on the received gas data, whether a gas leak is present in the received spatial location to the desired level of confidence. If a gas leak is not detected, no immediate action is needed and further tests may be accomplished in the future to ensure that no gas leaks develop. If a gas leak is detected, then corrective action may be taken to minimize and/or stop the gas leak.

In some embodiments, the processor 802 may be in communication with addressable memory 830. The memory may store the result of whether a gas leak was detected, historical gas data, the received spatial location 804, potential gas sources 806, 808, 810, level of confidence 812, wind data 814, and/or portable device 836 information. In some embodiments, the processor 802 may be in communication with an additional processor 832. The additional processor 832 may be a part of the portable device 836, a cloud computing device, a controller used to control the portable device 836, or the like.

Figure 9:
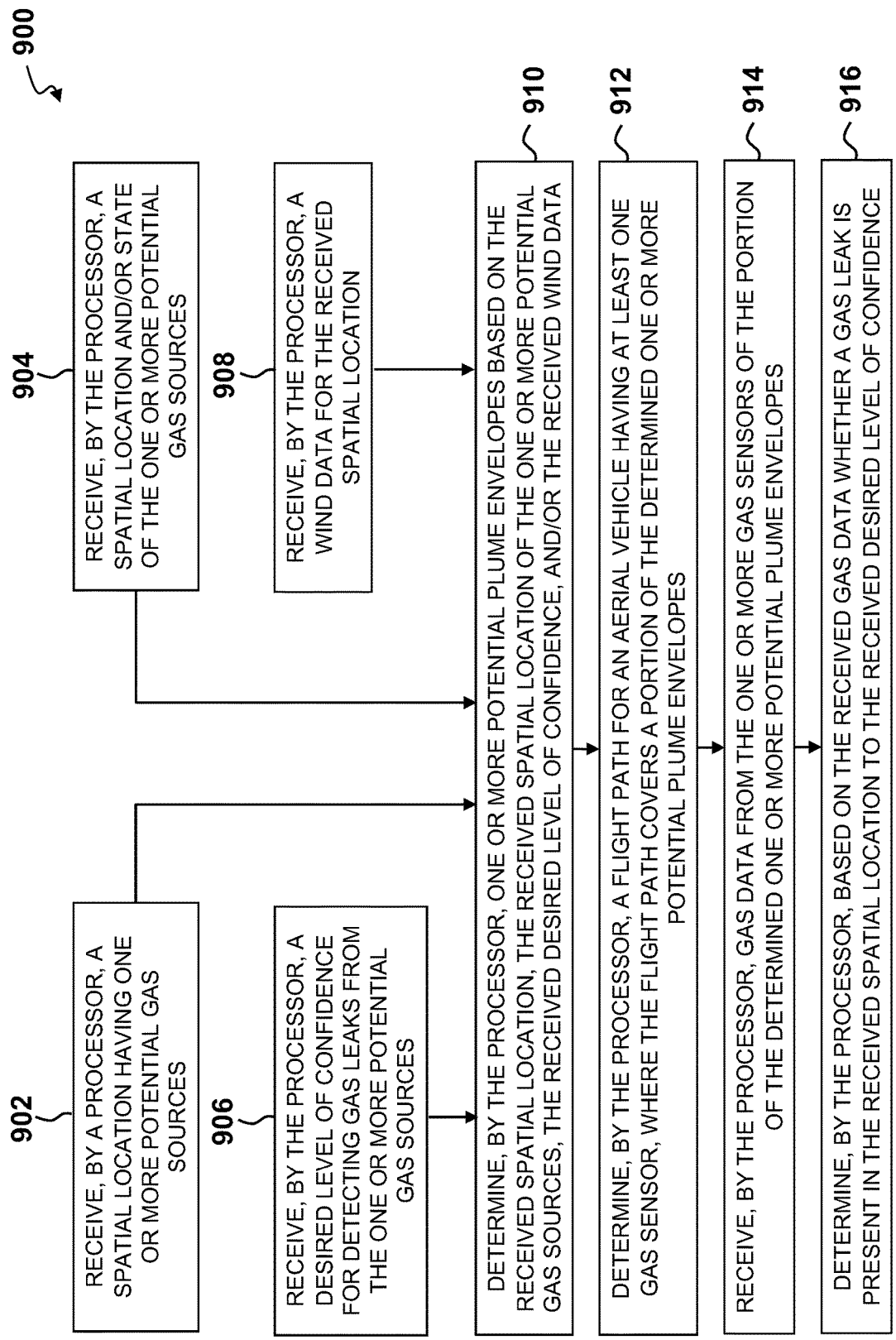
FIG. 9 depicts a high-level flowchart of a method embodiment of determining a likelihood of gas leaks within a spatial location, according to one embodiment

FIG. 9 depicts a high-level flowchart of a method embodiment 900 of determining a likelihood of gas leaks within a spatial location, according to one embodiment. The method 900 may include receiving, by a processor having addressable memory, a spatial location having one or more potential gas sources (step 902). The method 900 may then include receiving, by the processor, a spatial location and/or state of the one or more potential gas sources (step 904). In some embodiments, the state of the potential gas source, i.e., on or off, may be communicated. For some potential gas sources, being in an off state could drop the potential for a gas leak to zero or close to zero. For example, a potential gas source in an off position could have no potential plume enveloped associated with the off potential gas source. The method 900 may then include receiving, by the processor, a desired level of confidence for detecting gas leaks from the one or more potential gas sources (step 906).

The method 900 may then include receiving, by the processor, a wind data for the received spatial location (step 908). The wind data may include a wind speed and a wind direction. In some embodiments, the wind data may include multiple wind speeds and wind directions. In some embodiments, the wind data may include historical wind directions and wind speeds. In some embodiments, the wind data may include predicted future wind directions and wind speeds. These four inputs (902, 904, 906, 908) may be received in any order. In some embodiments, the received spatial location (step 902) may be inferred from the received spatial location and/or state of the one or more potential gas sources (step 904).

The method 900 may then include determining, by the processor, one or more potential plume envelopes based on the received spatial location, the received spatial location of the one or more potential gas sources, the received desired level of confidence, and/or the received wind direction and wind speed (step 910). The method 900 may then include determining, by the processor, a flight path for an aerial vehicle having at least one gas sensor, where the flight path covers the determined one or more potential plume envelopes (step 912). In some embodiments, the aerial vehicle may not be able to cover an entire portion of the plume envelope due to flight restrictions, access constraints, or the like. In some embodiments, the flight path may be modified if the entire portion of the plume envelope cannot be covered. For example, the desired level of confidence may be lowered, the flight time may be increased, the flight path may be modified, or the like in response to a restriction on covering the entire portion of the plume envelope. While an aerial vehicle is described, in some embodiments, the gas sensor may be mounted on a robot, a handheld device, or the like.

The method 900 may then include receiving, by the processor, gas data from the one or more gas sensors of the determined one or more potential plume envelopes (step 914). The method 900 may then include determining, by the processor, based on the received gas data whether a gas leak is present in the received spatial location to the received desired level of confidence (step 916).

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A system comprising:
  a processor having addressable memory, the processor configured to:
    receive a spatial location of one or more potential gas sources;
    receive a wind data for the received spatial location;
    determine a flight envelope encompassing one or more potential plume envelopes based the received spatial location of the one or more potential gas sources and the received wind data.

2. The system of claim 1, further comprising:
  an aerial vehicle; and
  at least one trace-gas sensor disposed on the aerial vehicle, the trace-gas sensor configured to generate gas data.

3. The system of claim 2, further comprising:
  a navigation system disposed on the aerial vehicle to determine a location of the at least one trace-gas sensor.

4. The system of claim 3, wherein the navigation system is a global positioning system.

5. The system of claim 2, wherein the processor is further configured to:
  receive a desired level of confidence for detecting gas leaks from the one or more potential gas sources.

6. The system of claim 5, wherein determining the flight envelope encompassing the one or more potential plume envelopes is further based on the received desired level of confidence.

7. The system of claim 6, wherein the processor is further configured to:
  determine a flight path for the aerial vehicle, wherein the flight path covers a portion of the determined flight envelope.

8. The system of claim 7, wherein the processor is further configured to:

receive the gas data from the at least one trace-gas sensors of the portion of the determined flight envelope.

9. The system of claim 8, wherein the processor is further configured to:
determine based on the received gas data whether a gas leak is present in the received spatial location to the received desired level of confidence.

10. A method comprising:
receiving, by a processor having addressable memory, a spatial location of one or more potential gas sources;
receiving, by the processor, a wind data for the received spatial location;
determining, by the processor, a flight envelope encompassing one or more potential plume envelopes based on the received spatial location of the one or more potential gas sources and the received wind data.

11. The method of claim 10, further comprising:
receiving, by the processor, a desired level of confidence for detecting gas leaks from the one or more potential gas sources.

12. The method of claim 11, wherein determining the flight envelope encompassing the one or more potential plume envelopes is further based on the received desired level of confidence.

13. The method of claim 12, further comprising:
determining, by the processor, a flight path for an aerial vehicle having at least one trace-gas sensor, wherein the flight path covers a portion of the determined flight envelope.

14. The method of claim 13, further comprising:
receiving, by the processor, gas data from the at least one trace-gas sensors of the portion of the determined flight envelope.

15. The method of claim 14, further comprising:
determining, by the processor, based on the received gas data whether a gas leak is present in the received spatial location to the received desired level of confidence.

16. A system comprising:
a portable device;
at least one trace-gas sensor disposed on the portable device, the trace-gas sensor configured to generate gas data;
a navigation system disposed on the portable device to determine a location of the at least one trace-gas sensor; and
a processor having addressable memory, the processor configured to:
receive a spatial location of one or more potential gas sources;
receive a wind data for the received spatial location;
determine a vehicle trajectory encompassing one or more potential plume envelopes based on the received spatial location of the one or more potential gas sources and the received wind data.

17. The system of claim 16, wherein the processor is further configured to:
receive a desired level of confidence for detecting gas leaks from the one or more potential gas sources, wherein determining the vehicle trajectory encompassing the one or more potential plume envelopes is further based on the received desired level of confidence.

* * * * *